Jan. 15, 1952 C. G. DUEHRSEN Plant Pat. 1,066
ROSE PLANT
Filed Oct. 9, 1950
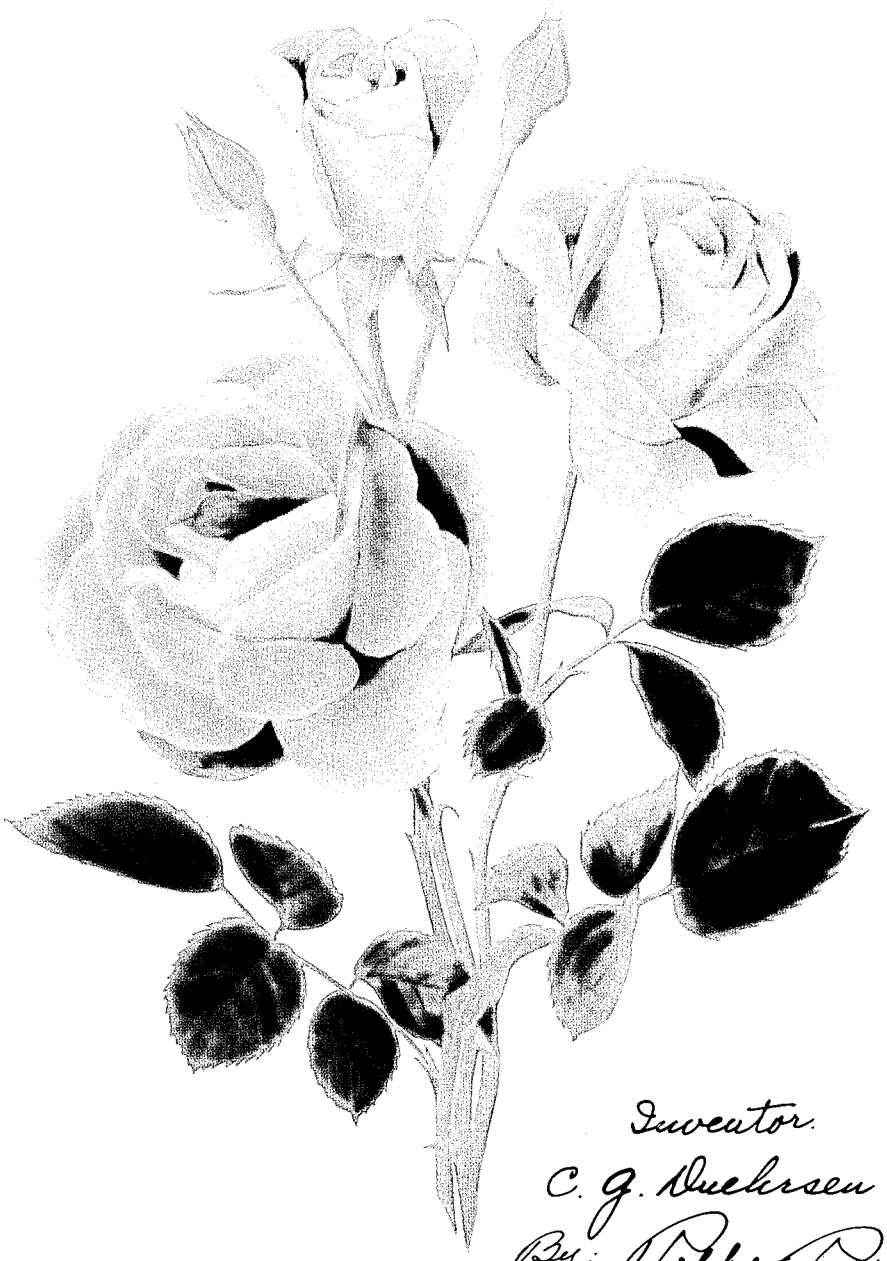
Inventor.
C. G. Duehrsen
By: Robbins Cobb
Attorneys.

Patented Jan. 15, 1952

Plant Pat. 1,066

UNITED STATES PATENT OFFICE 1,066

ROSE PLANT

Carl G. Duehrsen, Montebello, Calif., assignor to Constance A. Elmer, trading as Elmer Roses, San Gabriel, Calif.

Application October 9, 1950, Serial No. 189,155

1 Claim. (Cl. 47—61)

This invention relates to a new and distinct variety of rose plant of the hybrid floribunda class, originated by crossing an unnamed seedling with the variety "Margy" (unpatented).

As the result of this cross, I have produced a new variety of rose plant which is not only distinct from either parent, but is unlike any other polyantha or floribunda rose of which I am aware, in respect to size, habit and color of flowers, although it most closely resembles the climbing rose "Billy Boiler" (unpatented) in the color of its flowers.

This new variety is endowed with a unique combination of characteristics which are particularly desirable and advantageous for both decorative garden use and for cut flowers, and materially contribute to its attractiveness. Among its important and dominant characteristics are the following:

(1) In habit of growth, the new variety is exceptionally vigorous, upright, relatively free of prickles, but with a small number of thorns on its bright green stems;

(2) Its type falls between the polyantha class and the hybrid tea class and represents a remarkable combination of cluster-flowering habit of polyanthas with large flower size of the hybrid teas;

(3) The flowers of the new variety are an unusually uniform shade of bright Indian Lake red of remarkable lasting color quality, having almost the same color in the older flowers as when first open, this lack of fading and the fact that the flowers are borne on relatively long cutting stems, making the variety especially adapted for cut flowers; and (4) The petals of the flowers drop off cleanly.

Asexual reproduction of this new variety both by cuttings and by budding at Montebello, California, shows that the foregoing characteristics come true to form and are established and transmitted through succeeding propagations.

The accompanying drawing shows specimens of the new variety, with their foliage and flowers in different stages of development.

The following is a detailed description of the new variety, with color terminology in accordance with the Horticultural Color Chart of the British Color Council, except where general color terms of ordinary dictionary significance are obvious:

Parentage: Seedling.
*Seed parent.*—An unnamed seedling.
*Pollen parent.*—"Margy."

Type: Relatively hardy; tall; bush; for outdoor garden decoration and for cut flowers.
Class: Large-flowered Hybrid Floribunda.
Propagation: Holds its distinguishing characteristics through succeeding propagations by cuttings and budding.

*Flower*

Locality where grown: San Gabriel, California.
Continuity: Continuous.
Fragrance: Slight; sweetbriar.
Flowers borne: Occasionally singly, sometimes two or three, but usually several, to stem; in irregular cluster; on strong, long stems.
Quantity of bloom: Abundant; outdoors.
Bud:
Peduncle.—Short; medium heavy; erect; stiff; green; relatively smooth, but having a variable number of inconspicuous small grey hairs and very small soft thorns; some peduncles being almost completely free of either hairs or thorns.
*Before calyx breaks.*—Size—medium. Form—short; oval; without foliaceous appendages on the surface of the bud; but with alternate sepals having two to three small lance-shaped appendages about one-eighth to one-fourth inch long on margins and without foliaceous parts extending beyond the tip of the bud. Color—Dahlia Purple (931).
*As calyx breaks.*—Color—Dahlia Purple (931).
*As first petal opens.*—Size—medium. Form—medium long; ovoid. Color—outside: Chrysanthemum Crimson (824/1); inside: near Indian Lake (826), but brighter.
*Opening.*—Opens up well. Is not retarded from opening by hot, dry weather.
Bloom:
*Size, when fully open.*—Medium; 3½ inches to 4 inches.
*Petalage.*—Semi-double (2 or even 3 rows), but the stamens not hidden; from 28 to 34 petals, arranged irregularly.
*Form.*—High centered becoming open; petals being at first tightly rolled inward, and later becoming slightly rolled outward, thus covering for the most part the stamens, and giving a pleasing effect of more petalage to the flower; becoming still later, at maturity, loosely rolled outward.
Petals: Thick; leathery; with inside velvety and outside satiny.

*Shape.*—Outside—entirely round to obovate with one notch in center. Intermediate—round to obovate, but more narrow and with one notch only in center; occasional inner petal ovate to ovate-lanceolate. Inside—round to obovate with one notch.

*Color.*—Colors may be modified by being shaded with other colors, occasionally deepened by dark almost black shadows, but remarkably uniform in general with no borders or margins of other color.

This description of a newly opened flower was made from a rose grown outdoors in the month of August, 1950, at San Gabriel, California:

*Color.* — Outside petal — outside surface: Chrysanthemum Crimson, Plate 824/2; inside surface: Indian Lake, Plate 826/1. Intermediate petal — outside surface: Chrysanthemum Crimson, Plate 824/2; inside surface: Indian Lake, Plate 826/1. Inner petal—outside surface: Chrysanthemum Crimson, Plate 824/2; inside surface: Indian Lake, Plate 826/1.

This description was made from a rose that was open for three days outdoors in the month of August, 1950, at San Gabriel, California:

*Color.* — Outside petal — outside surface: Chrysanthemum Crimson, Plate 824/3; inside surface: Indian Lake, Plate 826/1. Inside petal — outside surface: Chrysanthemum Crimson, Plate 824/3; inside surface: Indian Lake, Plate 826/1.

*General color effect.*—Newly opened flower — Chrysanthemum Crimson, Plate 824/3. Three days open—Indian Lake, Plate 826/1.

*Behavior.*—Drop off cleanly; non-fading; no ill effects in 18° low, 98° high.

*Flower longevity.*—On bush in garden—4 to 5 days in August. Cut roses grown outdoors, kept at living-room temperatures—3 to 4 days in August.

*Reproductive organs*

Stamens: Many, arranged regularly about pistils; and not mixed with pistils or with petaloids.
Filaments: Medium length; most with anthers. Color—Begonia (619).
Anthers: Small to medium; open at various times. Color—Orange Buff, Plate 507/2.
Pollen: Moderate to abundant; golden yellow.
Pistils: Many.
Styles: Very uneven; medium length; thin; bunched, and upper part of many sharply bent.
Stigma: Color—Yellow.

Ovaries: All enclosed in calyx.
Hips: Short; globular; green-gray; smooth; walls fleshy.
Sepals: Falling soon; moderately long; spear-shaped. Color—dark green.
Seeds: Many, medium size.

*Plant*

Foliage:

*Leaves.*—Compound of three to five leaflets; normal abundance; large; leathery and somewhat glossy.

*Leaflets.*—Shape—oval with apex acute; base—round; margin—simply serrate.

*Color.*—Mature—upper surface: dark green with conspicuous reddish veins; under surface — gray-green. Young — upper surface: dark green with conspicuous reddish veins; under surface—gray-green.

*Rachis.*—Medium heavy. Upper side—grooved; hairy; under side—smooth.

*Stipules.*—Medium length; medium width; with short points turning out at an angle of less than 45°.

*Disease.*—Resistant to mildew and blackspot.

Growth:

*Habit.*—Bushy; upright.
*Growth.*—Vigorous.
*Canes.*—Heavy.
*Main stems.*—Green. *Thorns*—few; medium length; hooked downward; with broad oval base. *Prickles and hairs*—none.
*Branches.* — Green. *Thorns* — few; short; hooked downward; with broad oval base. *Prickles*—few; reddish. *Hairs*—none.
*New shoots.*—Bright green. *Thorns*—few; short; hooked downward; with broad base. *Prickles*—few; reddish. *Hairs*—none.

I claim:

A new and distinct variety of rose plant of the hybrid floribunda class, characterized as to novelty by its vigorous and upright habit of growth, by its relative freedom from prickles and few thorns on its bright green stems, by the cluster-flowering habit of its large-size flowers borne on long stems, by the uniform, long-lasting and non-fading bright Indian Lake red color of its flowers, and by the cleanly dropping habit of its flower petals, substantially as herein shown and described.

CARL G. DUEHRSEN.

No references cited.